United States Patent
Florence et al.

(10) Patent No.: US 11,266,594 B2
(45) Date of Patent: *Mar. 8, 2022

(54) TOPICAL SKIN CARE FORMULATIONS COMPRISING PLANT EXTRACTS

(71) Applicant: MARY KAY INC., Addison, TX (US)

(72) Inventors: Tiffany Florence, Dallas, TX (US); Michelle Hines, Hickory Creek, TX (US)

(73) Assignee: MARY KAY INC., Addison, TX (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/854,160

(22) Filed: Apr. 21, 2020

(65) Prior Publication Data

US 2020/0246249 A1 Aug. 6, 2020

Related U.S. Application Data

(63) Continuation of application No. 15/987,607, filed on May 23, 2018, now Pat. No. 10,660,845, which is a continuation of application No. 15/297,550, filed on Oct. 19, 2016, now Pat. No. 10,004,680, which is a continuation of application No. 14/949,259, filed on Nov. 23, 2015, now Pat. No. 9,498,428, which is a continuation of application No. 13/821,896, filed as application No. PCT/US2011/048834 on Aug. 23, 2011, now Pat. No. 9,220,675.

(60) Provisional application No. 61/381,306, filed on Sep. 9, 2010.

(51) Int. Cl.
| | |
|---|---|
| A61K 36/18 | (2006.01) |
| A61K 8/9789 | (2017.01) |
| A61Q 19/00 | (2006.01) |
| A61Q 19/02 | (2006.01) |
| A61Q 19/08 | (2006.01) |
| A61K 8/97 | (2017.01) |
| A61K 8/06 | (2006.01) |
| A61K 8/04 | (2006.01) |

(52) U.S. Cl.
CPC ............ *A61K 8/9789* (2017.08); *A61K 8/042* (2013.01); *A61K 8/06* (2013.01); *A61K 8/062* (2013.01); *A61K 8/97* (2013.01); *A61K 36/18* (2013.01); *A61Q 19/007* (2013.01); *A61Q 19/02* (2013.01); *A61Q 19/08* (2013.01); *A61K 2800/782* (2013.01); *A61K 2800/80* (2013.01)

(58) Field of Classification Search
None
See application file for complete search history.

(56) References Cited

U.S. PATENT DOCUMENTS

| | | | |
|---|---|---|---|
| 4,505,740 A | 3/1985 | Hatton et al. | |
| 4,879,376 A | 11/1989 | Foresta et al. | |
| 5,660,865 A | 8/1997 | Pedersen et al. | |
| 5,859,343 A | 1/1999 | Sun et al. | |
| 6,051,758 A | 4/2000 | Sun et al. | |
| 6,217,874 B1 | 4/2001 | Johannsen | |
| 6,280,751 B1 | 8/2001 | Fletcher et al. | |
| 6,399,089 B1 | 6/2002 | Yegorova et al. | |
| 6,406,720 B1 | 6/2002 | Pauly et al. | |
| 6,462,041 B1 | 10/2002 | Cai et al. | |
| 6,485,759 B2 | 11/2002 | Chantara et al. | |
| 6,613,762 B2 | 9/2003 | Cai et al. | |
| 7,172,772 B2 | 2/2007 | Pushpangadan et al. | |
| 7,182,964 B2 | 2/2007 | Kupper et al. | |
| 7,381,430 B2 | 6/2008 | Lai et al. | |
| 7,459,288 B2 | 12/2008 | Bosley et al. | |
| 7,517,852 B2 | 4/2009 | Walsh et al. | |
| 7,622,497 B2 | 11/2009 | Cai et al. | |
| 8,828,455 B2 | 9/2014 | Florence et al. | |
| 8,877,259 B2 | 11/2014 | Florence et al. | |
| 9,220,675 B2 | 12/2015 | Florence et al. | |
| 9,278,061 B2 | 3/2016 | Florence et al. | |
| 9,358,203 B2 | 6/2016 | Florence et al. | |
| 10,660,845 B2 * | 5/2020 | Florence .................. | A61K 8/06 |
| 2003/0068393 A1 | 4/2003 | Arkhurst et al. | |
| 2003/0078292 A1 | 4/2003 | Cai et al. | |
| 2004/0082066 A1 | 4/2004 | Cai et al. | |
| 2004/0197429 A1 | 10/2004 | Obukowicz et al. | |
| 2005/0163815 A1 | 7/2005 | Bowen et al. | |
| 2005/0267047 A1 | 12/2005 | Jia et al. | |
| 2006/0148732 A1 | 7/2006 | Gutterman et al. | |
| 2007/0020304 A1 | 1/2007 | Tamarkin et al. | |
| 2007/0093456 A1 | 4/2007 | Cai et al. | |
| 2007/0196528 A1 | 8/2007 | Bonnet et al. | |

(Continued)

FOREIGN PATENT DOCUMENTS

| | | |
|---|---|---|
| CN | 1524587 | 9/2004 |
| WO | WO 2009/086595 | 7/2009 |

OTHER PUBLICATIONS

A.P. Mouzou et al. "Effets du decocte de Biophytum petersianum (Oxalidaceae) sur la liberation du calcium du reticulum sarcoplasmique des cellules musculaires squelettiques", Phytotherapie vol. 8, No. 4 (2010): 231-235.
Adeniyi (Afr. J. Med. Sci. (1996), vol. 25, pp. 221-224).
Ajaiyeoba and Krebs, "Antibacterial and Antifungal activities of *Quassia undulata* and *Quassia amara* extracts in vitro," *Afr. J. Med. Med. Sci.* 2003; 32: 353-356.
Dweck et al. "The internal and external use of medicinal plants", Clinics in Dermatology vol. 27, No. 2 (2009): 153, 156-157.
E.O. Ajaiyeoba et al. "In vivo antimalarial activities of *Quassia amara* and *Quassia undulate* plant extracts in mice", Journal of Ethnopharmacology vol. 67, No. 3 (1999): 321-325.

(Continued)

*Primary Examiner* — Susan Hoffman
(74) *Attorney, Agent, or Firm* — Norton Rose Fulbright US LLP

(57) ABSTRACT

A method of treating a skin condition resulting from exposure to pollution or free radicals is disclosed. The method can include topically applying to skin having the skin condition a composition comprising an effective amount of an extract of *Diospyros mespiliformis* leaf to reduce oxidative damage in the skin having the skin condition.

20 Claims, No Drawings

(56) References Cited

U.S. PATENT DOCUMENTS

| | | |
|---|---|---|
| 2007/0259056 A1 | 11/2007 | Bowen et al. |
| 2007/0264363 A1 | 11/2007 | Bowen et al. |
| 2008/0081056 A1 | 4/2008 | Nussinovitch et al. |
| 2008/0089958 A1 | 4/2008 | Diehl et al. |
| 2008/0132581 A1 | 6/2008 | Jia et al. |
| 2009/0074822 A1 | 3/2009 | Declercq et al. |
| 2009/0081133 A1 | 3/2009 | Bottoni et al. |
| 2009/0124694 A1 | 5/2009 | Bosley et al. |
| 2009/0163577 A1 | 6/2009 | Reed et al. |
| 2009/0258097 A1 | 10/2009 | Pretorius |
| 2009/0275472 A1 | 11/2009 | Pretorius |

OTHER PUBLICATIONS

International Preliminary Report on Patentability issued in PCT Application No. PCT/US2011/048834, dated Mar. 12, 2013.
International Search Report and Written Opinion issued in PCT Application No. PCT/US2011/048834, dated Feb. 26, 2013.
K. Venkata Ratnam et al. "Traditional Medicine Used by the Adivasis of Eastern Ghats, Andhra Pradesh—For Bone Fractures", Ethnobotanical Leaflets International Web Journal vol. 12 (2008): 19-22.
Liu & Zhou, "Organic Chemistry Experiment" Wuhan University of Technology Press, $1^{st}$ Edition, 2009, Aug. 31, 2009. (English Translation).
Office Action issued in corresponding Chinese Patent Application No. 201610548372.7, dated Mar. 19, 2019. (English Translation).
S.C. Chhabra et al. "Plants used in traditional medicine in Eastern Tanzania. V. Angiosperms (Passifloraceae to Sapindaceae)", Journal of Ethnopharmacology vol. 33, No. 1-2 (1991): 143-157.
Tom Erik Grønhaug et al. "Ethnopharmacological survey of six medicinal plants from Mali, West-Africa", Journal of Ethnobiology and Ethnomedicine vol. 4, No. 1 (2008): 26.
Wyatt et al., "Phytochemical Analysis and Biological Screening of Leaf and Twig Extracts from *Kunzea ericoides*," *Phytotherapy Research*, 2005, 19:963-970.

* cited by examiner

TOPICAL SKIN CARE FORMULATIONS COMPRISING PLANT EXTRACTS

CROSS REFERENCE TO RELATED APPLICATIONS

This application is a continuation of U.S. patent application Ser. No. 15/987,607, filed May 23, 2018, now U.S. Pat. No. 10,660,845, which is a continuation of U.S. Patent Application Ser. No. 15/297,550, filed Oct. 19, 2016 (U.S. Pat. No. 10,004,680), which is a continuation of U.S. patent application Ser. No. 14/949,259, filed Nov. 23, 2015 (U.S. Pat. No. 9,498,428), which is a continuation of U.S. patent application Ser. No. 13/821,896, filed Apr. 19, 2013 (U.S. Pat. No. 9,220,675), which is a national phase application of PCT/US2011/048834 filed Aug. 23, 2011, which claims the benefit of U.S. Provisional Application No. 61/381,306, filed Sep. 9, 2010. The contents of the referenced applications are incorporated into the present application by reference.

BACKGROUND OF THE INVENTION

Field of the Invention

The present invention relates generally to compositions that include one or any combination of extracts from the following plants: *Kunzea ericoides; Quassia undulata; Diospyros mespiliformis; Khaya senegalensis; Biophytum petersianum; Detarium microcarpum; Crossopteryx febrofiga; Allophylus africanus; Burkea africana; Nauclea latifolia; Bombax costatum; Buchanania reticulata; Melanorrhoea laccifera; Machilus odoratissimus; Spondias pinnata; Canthium dicoccum; Parinari annamensis; Aporosa tetrapleura; Knema globularia; Garcinia gaudichaudii; Randia dasycarpa; Capparis micrantha;* or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts. The extracts can be from the whole plant (i.e., the entire plant is used to prepare the extract) or from a part of the plant (e.g., leaf, stem, root, flower, seed, bark, fruit, sap, etc.). The compositions can be formulated as topical skin compositions, edible compositions, injectible compositions, oral compositions, hair care compositions, etc.

Description of Related Art

Ageing, chronic exposure to adverse environmental factors, malnutrition, fatigue, etc., can change the visual appearance, physical properties, or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Previous attempts to improve the visual appearance of skin with known skin active-ingredients have been shown to have various drawbacks such as skin irritation and prolonged recovery periods.

SUMMARY OF THE INVENTION

The inventors discovered that a wide variety of plant extracts have therapeutic benefits. These extracts include extracts obtained from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifiga, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha,* or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts. The extracts can be from the whole plant (i.e., the entire plant is used to prepare the extract) or from a part of the plant (e.g., leaf, stem, root, flower, seed, bark, fruit, sap, etc.). The compositions can be formulated as topical skin compositions, edible compositions, injectible compositions, oral compositions, hair care compositions, etc. In particular aspects, the combinations of (1) *Quassia undulate* and *Melanorrhoea laccifera*, (2) *Quassia undulata, Buchanania reticulata,* and *Canthium dicoccum,* and/or (3) *Quassia undulata, Aporosa tetrapleura,* and *Canthium dicoccum* have been found to work well in providing a multi-functional/multi beneficial skin treatment composition, as such combinations provide a wide range of benefits ranging from COX-1 inhibition, COX-2 inhibition, antioxidant activity, MMP-1 inhibition, lipoxygenase inhibition, tyrosinase inhibition, TNF-$\alpha$ inhibition, stimulation of collagen synthesis, and B16 melanogenesis inhibition. In other aspects, the following combinations have also been shown to work well for a multi-beneficial/multi-purpose skin treatement composisition: The extracts can be aqueous extracts, non-aqueous extracts, lyophilized extracts, etc. The extracts can be extracted with alcohol (e.g., methanol, ethanol propanol, butanol, etc.), glycols (e.g., propylene glycol, butylene glycol, etc.), oils, water, etc. The compositions of the present invention are capable of inhibiting COX-1, COX-2, MMP-1, lipoxygenase, tyrosinase, TNF-$\alpha$, and/or B16 melanogenesis enzymes, stimulating collagen synthesis, and/or activating the binding site of alpha-2 adrenergic receptors. Additional combinations that were discovered that can be useful for multi-purpose/multi-beneficial compositions to treat skin include a combination of *Kunzea ericoides* leaf extract, *Quassia undulata* leaf extract, and *Garcinia gaudichaudii* leaf extract, which results in a composition that has a wide variety of benefits such as inhibition of COX-1, COX-2, MMP-1, lipoxygenase, tyrosinase, TNF-$\alpha$, and B16 melanogenesis enzymes, while also stimulating collagen synthesis and activating the binding site of alpha-2 adrenergic receptors, and further comprising anti-oxidant effects. Therefore, such a combination can be used to create a multi-purpose composition (e.g., skin treatment, disease, food, etc.). In another aspect, the combination of *Quassia undulata* leaf, *Buchanania reticulata* leaf, *Canthium dicoccum* leaf, and *Randia dasycarpa* leaf extract surprising provides a wide variety of benefits such as inhibition of COX-1, COX-2, MMP-1, lipoxygenase, tyrosinase, TNF-$\alpha$, and B16 melanogenesis enzymes, while also stimulating collagen synthesis and activating the binding site of alpha-2 adrenergic receptors, and further comprising anti-oxidant effects.

The compositions can further include 0.01% to 99% by weight of said extracts (or 0.1, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30, 40, 50, 60, 70, 80, 90, 99%, or more or any integer or range therein). The composition can be formulated as a lotion, cream, gel, serum, emulsion, powder, etc. In certain instances, the compositions can further include a moisturizing agent or a humectant, water, a surfactant, a silicone containing compounds, a UV agent, an oil, an antioxidant, a vitamin or mineral, a structuring agent, a thickening agent, a cosmetic ingredient, a pharmaceutical ingredient, and/or other ingredients identified in this specification or those known in the art.

In another aspect, there is disclosed an aqueous extract, an oil extract, an alcoholic extract, a lyophilized extract from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha,* or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the plants. In particular aspects, the extracts are obtained from the whole plant (i.e., the entire plant is used to prepare the extract) or from a part of the plant (e.g., leaf, stem, root, flower, seed, bark, fruit, sap, etc.). In certain aspects, the extracts are obtained from the leaf, bark, or root. Such extracts can be incorporated into topical skin or hair care compositions, pharmaceutical compositions, edible compositions, food-based products, injectible compositions, etc. The compositions can be formulated as emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (e.g., aqueous or hydro-alcoholic solutions), anhydrous bases (e.g., lipstick or a powder), gels, ointments, milks, pastes, aerosols, solid forms, eye jellies, pills, liquid gel caps, etc. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.).

The compositions of the present invention can include any desired amount of any one of or any combination of the aforementioned extracts. The amount of the extracts can individually or combined be from 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 95, 96, 97, 98, 99%, or more, or any range derivable therein, by weight or volume of the extract or combination of extracts.

The compositions of the present invention can also be modified to have a desired oxygen radical absorbance capacity (ORAC) value. In certain non-limiting aspects, the compositions of the present invention or the plant extracts identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In another embodiment, there is disclosed a topical skin care composition that includes an one of or combination of the aforementioned extracts in combination with any one of, any combination of, or all of the following ingredients: water; glycerin; butylene glycol; propylene glycol; phenoxyethanol; a chelating agent (e.g., EDTA, disodium EDTA, trisodium EDTA, EGTA, disodium EGTA, trisodium EGTA, citric acid, phosphoric acid, succinic acid, etc.); steareth-20; chlorhexidine diglunonate; potassium sorbate; and/or a preservative (e.g., methylparaben, propylparaben, butylparaben, ethylparaben, isobutylparaben, etc.). In particular aspects, the composition can further include any one of, any combination of, or all of the following additional ingredients: alcohol; denatured alcohol; glyceryl stearate; dimethicone; PEG-100 stearate; capryl glycol; triethanolamine; maltodextrin; sorbic acid; ethylene brassylate; methyl linalool; isobutyl methyl tetrahydropyranol; ethylhexylglycerin; and/or hexylene glycol. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water.

In another embodiment, there is disclosed a topical skin care composition that includes an one of or combination of the aforementioned extracts in combination with any one of, any combination of, or all of the following ingredients: water; dimethicone; triethanolamine; phenonip; betaine; a chelating agent (e.g., EDTA, disodium EDTA, trisodium EDTA, EGTA, disodium EGTA, trisodium EGTA, citric acid, phosphoric acid, succinic acid, etc.); tocopheryl acetate; and/or prodew 400. In particular aspects, the composition can further include any one of, any combination of, or all of the following additional ingredients: propylene glycol; isododecane; polyacrylamide/C13-C14 isoparaffin/laureth 7 mixture; PEG-12 dimethicone; and/or ethylhexyl palmitate. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water.

In another embodiment, there is disclosed a topical skin care composition that includes an one of or combination of the aforementioned extracts in combination with any one of, any combination of, or all of the following ingredients: water; glycerin; pentylene glycol; capryl glycol; disodium EDTA; capric/caprylic triglyceride; shea butter; squalane; cetyl alcohol; dimethicone; ceramide II; stearic acid; a mixture of glyceryl stearate and PEG 100 stearate; or a mixture of acrylamide/acryloyl dimethyl taurate copolymer, isohexadecane, and polysorbate 80. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to glycerin can be from about 7:1 to 9:1 based on the total weight of the composition. The ratio of glycerin to pentylene glycol can be from about 1:1 to about 2:1 based on the total weight of the composition.

In another embodiment, there is disclosed a topical skin care composition that includes any one of or combination of the aforementioned extracts in combination with any one of, any combination of, or all of the following ingredients: water; glycerin; capryl glycol; capryl glycol; disodium EDTA; petrolatum; squalane; cetyl alcohol; a mixture of glyceryl stearate and PEG 100 stearate; dimethicone; or a mixture of acrylamide/acryloyl dimethyl taurate copolymer, isohexadecane, and polysorbate 80. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to glycerin can be from about 12:1 to 16:1 based on the total weight of the composition. The ratio of glycerin to pentylene glycol can be from about 0.5:1 to about 1.5:1 based on the total weight of the composition.

In another embodiment, there is disclosed a topical skin care composition that includes an one of or combination of the aforementioned extracts in combination with any one of, any combination of, or all of the following ingredients: water; xanthan gum; disodium EDTA; pentylene glycol; capryl glycol; acrylate C10-30 acrylate cross polymer; triethanolamine; PVP/hexadecene copolymer; C12-15 alkyl benzoate; sorbitan isostearate; or a sunscreen agent. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to C12-15 alkyl benzoate can be from about 2:1 to 3:1 based on the total weight of the composition. The ratio of water to pentylene glycol can be from about 9:1 to about 11:1 based on the total weight of the composition.

In another embodiment, there is disclosed a topical skin care composition that includes an one of or combination of the aforementioned extracts in combination with any one of, any combination of, or all of the following ingredients: water; disodium EDTA; citric acid; pentylene glycol; capryl glycol; sodium cocoamphodiacetate; or sodium methyl cocoyl taurate. The concentrations of these ingredients can range from 0.00001 to 99% by weight or volume of the composition or any integer or range derivable therein as explained in other portions of this specification which are incorporated into this paragraph by reference. In particular aspects, the concentration of water can be at least 35% to 80% by weight of water. The ratio of water to pentylene glycol can be from about 12:1 to 14:1 based on the total weight of the composition. The ratio of water to sodium cocoamphodiacetate can be from about 8:1 to about 11:1 based on the total weight of the composition. The ratio of water to sodium methyl cocoyl taurate can be from about 2:1 to about 4:1 based on the total weight of the composition. The ratio of sodium methyl cocoyl taurate to sodium cocoamphodiacetate can be from about 2:1 to about 4:1 based on the total weight of the composition.

In one non-limiting aspect of the present invention there is disclosed a method of treating skin comprising topically applying to skin in need thereof a compositing comprising an extract from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha,* or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts in a single composition, and a dermatologically acceptable vehicle, wherein topical application of the composition to skin in need thereof treats the skin condition. Such extracts can be from the whole plant or a part of the plant (e.g., leaf, stem, root, flower, seed, bark, fruit, sap, etc.). In particular instances, the extracts are from the leaf, bark and or root of the plant. The composition is capable of inhibiting COX-1, COX-2, MMP-1, lipoxygenase, tyrosinase, TNF-α, and/or B16 melanogenesis enzymes, stimulating collagen synthesis, and/or activating the binding site of alpha-2 adrenergic receptors. The composition can be applied to a fine line or wrinkle, erythemic skin, dry, flaky, or itchy skin, skin having an uneven skin tone or melasmic skin, inflamed skin, and other skin associated disorders disclosed throughout this specification. Erythema can be caused by skin sunburn, electrical treatments of skin, skin burns, contact allergies, systemic allergies, skin toxicity, exercise, insect stings, bacterial infection, viral infection, fungal infection, protozoa infection, massage, windburn, etc.

As noted above, the inventors surprisingly discovered various combinations of extracts that produce a wide range of skin benefits. Such combinations include: (1) *Quassia undulata* and *Melanorrhoea laccifera*; (2) *Quassia undulata*, *Buchanania reticulata*, and *Canthium dicoccum*; and/or (3) *Quassia undulata*, *Aporosa tetrapleura*, and *Canthium dicoccum*, which have been found to work well in providing a multi-functional/multi beneficial skin treatment composition, as such combinations provide a wide range of benefits ranging from COX-1 inhibition, COX-2 inhibition, antioxidant activity, MMP-1 inhibition, lipoxygenase inhibition, tyrosinase inhibition, TNF-α inhibition, stimulation of collagen synthesis, and B16 melanogenesis inhibition. Further combinations include *Kunzea ericoides* leaf extract, *Quassia undulata* leaf extract, and *Garcinia gaudichaudii* leaf extract results in a composition that has a wide variety of benefits such as inhibition of COX-1, COX-2, MMP-1, lipoxygenase, tyrosinase, TNF-α, and B16 melanogenesis enzymes, while also stimulating collagen synthesis and activating the binding site of alpha-2 adrenergic receptors.

In still another aspect of the present invention there is disclosed a method of treating dry, flaky, or itchy skin or reducing the appearance of uneven skin tone comprising topically applying a composition to dry, flaky, or itchy skin or to skin having an uneven skin tone, wherein the composition includes an extract selected from *Kunzea ericoides*, *Quassia undulata*, *Diospyros mespiliformis*, *Khaya senegalensis*, *Biophytum petersianum*, *Detarium microcarpum*, *Crossopteryx febrofiga*, *Allophylus africanus*, *Burkea africana*, *Nauclea latifolia*, *Bombax costatum*, *Buchanania reticulata*, *Melanorrhoea laccifera*, *Machilus odoratissimus*, *Spondias pinnata*, *Canthium dicoccum*, *Parinari annamensis*, *Aporosa tetrapleura*, *Knema globularia*, *Garcinia gaudichaudii*, *Randia dasycarpa*, *Capparis micrantha*, or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts in a single composition, and a dermatologically acceptable vehicle, wherein topical application of the composition to skin in need thereof treats the skin condition. Such extracts can be from the whole plant or a part of the plant (e.g., leaf, stem, root, flower, seed, bark, fruit, sap, etc.). In particular instances, the extracts are from the leaf, bark and or root of the plant. The composition is capable of inhibiting COX-1, COX-2, MMP-1, lipoxygenase, tyrosinase, TNF-α, and/or B16 melanogenesis enzymes, stimulating collagen synthesis, and/or activating the binding site of alpha-2 adrenergic receptors.

Also disclosed is a method of reducing the appearance of fine lines or wrinkles comprising topically applying a composition to skin having fine lines or wrinkles, wherein the composition includes an extract selected from the group consisting of: *Kunzea ericoides*, *Quassia undulata*, *Diospyros mespiliformis*, *Khaya senegalensis*, *Biophytum petersianum*, *Detarium microcarpum*, *Crossopteryx febrofiga*, *Allophylus africanus*, *Burkea africana*, *Nauclea latifolia*, *Bombax costatum*, *Buchanania reticulata*, *Melanorrhoea laccifera*, *Machilus odoratissimus*, *Spondias pinnata*, *Canthium dicoccum*, *Parinari annamensis*, *Aporosa tetrapleura*, *Knema globularia*, *Garcinia gaudichaudii*, *Randia dasycarpa*, *Capparis micrantha*, or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts in a single composition, and a dermatologically acceptable vehicle, wherein topical application of the composition to skin in need thereof treats the skin condition. Such extracts can be from the whole plant or a part of the plant (e.g., leaf, stem, root, flower, seed, bark, fruit, sap, etc.). In particular instances, the extracts are from the leaf, bark and or root of the plant. The composition is capable of inhibiting COX-1, COX-2, MMP-1, lipoxygenase, tyrosinase, TNF-α, and/or B16 melanogenesis enzymes, stimulating collagen synthesis, and/or activating the binding site of alpha-2 adrenergic receptors.

In one embodiment of the present invention there is disclosed a method of reducing the appearance of symptoms associated with erythema (e.g., erythemic skin, sensitive skin, inflamed skin) comprising topically applying a composition to erythemic, sensitive, or inflamed skin wherein the composition includes an extract selected from *Kunzea ericoides*, *Quassia undulata*, *Diospyros mespiliformis*, *Khaya senegalensis*, *Biophytum petersianum*, *Detarium microcarpum*, *Crossopteryx febrofiga*, *Allophylus africanus*, *Burkea africana*, *Nauclea latifolia*, *Bombax costatum*, *Buchanania reticulata*, *Melanorrhoea laccifera*, *Machilus odoratissimus*, *Spondias pinnata*, *Canthium dicoccum*, *Parinari annamensis*, *Aporosa tetrapleura*, *Knema globularia*, *Garcinia gaudichaudii*, *Randia dasycarpa*, *Capparis micrantha*, or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts in a single composition, and a dermatologically acceptable vehicle, wherein topical application of the composition to skin in need thereof treats the skin condition. Such extracts can be from the whole plant or a part of the plant (e.g., leaf, stem, root, flower, seed, bark, fruit, sap, etc.). In particular instances, the extracts are from the leaf, bark and or root of the plant. The composition is capable of inhibiting COX-1, COX-2, MMP-1, lipoxygenase, tyrosinase, TNF-α, and/or B16 melanogenesis enzymes, stimulating collagen synthesis, and/or activating the binding site of alpha-2 adrenergic receptors.

In a more general sense there is disclosed a method of treating or preventing a skin condition comprising topically applying a composition to skin having a skin condition, wherein the composition includes an extract selected from the group consisting of *Kunzea ericoides*, *Quassia undulata*, *Diospyros mespiliformis*, *Khaya senegalensis*, *Biophytum petersianum*, *Detarium microcarpum*, *Crossopteryx febrofiga*, *Allophylus africanus*, *Burkea africana*, *Nauclea latifolia*, *Bombax costatum*, *Buchanania reticulata*, *Melanorrhoea laccifera*, *Machilus odoratissimus*, *Spondias pinnata*, *Canthium dicoccum*, *Parinari annamensis*, *Aporosa tetrapleura*, *Knema globularia*, *Garcinia gaudichaudii*, *Randia dasycarpa*, *Capparis micrantha*, or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts in a single composition, and a dermatologically acceptable vehicle, wherein topical application of the composition to skin in need thereof treats the skin condition. Such extracts can be from the whole plant or a part of the plant (e.g., leaf, stem, root, flower, seed, bark, fruit, sap, etc.). In particular instances, the extracts are from the leaf, bark and or root of the plant. The composition is capable of inhibiting COX-1, COX-2, MMP-1, lipoxygenase, tyrosinase, TNF-α, and/or B16 melanogenesis enzymes, stimulating collagen synthesis, and/or activating the binding site of alpha-2 adrenergic receptors. The compositions described throughout the specification and claims can be used with this method. Non-limiting examples of skin conditions include dry skin, itchy skin, inflamed skin, erythema, sensitive skin, pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, sun burns, burned skin, open wounds, skin-inflammatory skin conditions, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of treating hyperpigmentation comprising applying the compositions of the present invention to the skin. The method can also comprise identifying a person in need of treating hyperpigmentation and applying the composition to a portion of the skin exhibiting hyperpigmentation. Additional methods contemplated by the inventors include methods for reducing the appearance of an age spot, a skin discoloration, or a freckle, reducing or preventing the appearance of fine lines or wrinkles in skin, or increasing the firmness of skin by applying the compositions of the present invention to skin in need of such treatment.

In yet another aspect of the present invention there is disclosed a method of treating or preventing a wide variety of diseases comprising administering to a patient in need of treatment a composition comprising an extract selected from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha*, or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts. Such extracts can be from the whole plant or a part of the plant (e.g., leaf, stem, root, flower, seed, bark, fruit, sap, etc.). In particular instances, the extracts are from the leaf, bark and or root of the plant. The composition is capable of inhibiting COX-1, COX-2, MMP-1, lipoxygenase, tyrosinase, TNF-α, and/or B16 melanogenesis enzymes, stimulating collagen synthesis, and/or activating the binding site of alpha-2 adrenergic receptors. The composition can be formulated as a topical composition, an ingestible composition, an injectible composition, an aerosolized composition, etc. Non-limiting examples of diseases that can be treated or prevented with such compositions include AIDS, autoimmune diseases (e.g., rheumatoid arthritis, multiple sclerosis, diabetes—insulin-dependent and non-independent, systemic lupus erythematosus and Graves disease), cancer (e.g., malignant, benign, metastatic, precancer), cardiovascular diseases (e.g., heart disease or coronary artery disease, stroke—ischemic and hemorrhagic, and rheumatic heart disease), diseases of the nervous system, and infection by pathogenic microorganisms (e.g., Athlete's Foot, Chickenpox, Common cold, Diarrheal diseases, Flu, Genital herpes, Malaria, Meningitis, Pneumonia, Sinusitis, Skin diseases, Strep throat, Tuberculosis, Urinary tract infections, Vaginal infections, Viral hepatitis), inflammation (e.g., allergy, asthma), prion diseases (e.g., CID, kuru, GSS, FFI), obesity, etc.

In even a further embodiment there is disclosed a method of treating or preventing hair loss comprising administering to a patient in need of treatment a composition comprising an extract selected from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha*, or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts in a single composition, and a pharmaceutically (whether topical, oral, injectible, etc.) or dermatologically acceptable vehicle, wherein administering to the patient in need thereof prevents or treats hair loss. Preventing or treating hair loss can include stimulating hair growth on the scalp, in eyebrows, in eyelashes, or on other regions of the body where hair growth is desired. Such extracts can be from the whole plant or a part of the plant (e.g., leaf, stem, root, flower, seed, bark, fruit, sap, etc.). In particular instances, the extracts are from the leaf, bark and or root of the plant. The composition is capable of inhibiting COX-1, COX-2, MMP-1, lipoxygenase, tyrosinase, TNF-α, and/or B16 melanogenesis enzymes, stimulating collagen synthesis, and/or activating the binding site of alpha-2 adrenergic receptors.

Also disclosed is a composition comprising an extract of *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha*, or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of the extracts in a single composition. The composition can take the form of a pill, liquid gel cap, or tablet. The composition can be an injectable solution (e.g., for intravenous delivery). The composition can be in the form of a neutraceutical. The extract can be an aqueous extract. The aqueous extract can include an alcohol, a glycol (e.g., butylene glycol, propylene glycol, or a combination thereof) water and/or oil.

In one instance there is disclosed a multi-functional topical skin care composition comprising: (a) ingredients comprising: (i) an inhibitor of COX-1 selected from the group consisting of: an extract of *Quassia undulate*; an extract of *Biophytum petersianum*; an extract of *Allophylus africanus*; an extract of *Buchanania reticulate*; an extract of *Melanorrhoea laccifera*; an extract of *Canthium dicoccum*; an extract of *Aporosa tetrapleura*; and any combination thereof; (ii) an inhibitor of COX-2 selected from the group consisting of: an extract of *Buchanania reticulate*; an extract of *Melanorrhoea laccifera*; an extract of *Aporosa tetrapleura*, and any combination thereof; (iii) an antioxidant selected from the group consisting of: an extract of *Quassia undulate*; an extract of *Biophytum petersianum*; an extract of *Buchanania reticulate*; an extract of *Melanorrhoea laccifera*; an extract of *Aporosa tetrapleura*; and any combination thereof; (iv) an inhibitor of MMP-1 selected from the group consisting of: an extract of *Quassia undulate*; an extract of *Buchanania reticulate*; an extract of *Melanorrhoea laccifera*; an extract of *Aporosa tetrapleura*; and any combination thereof; (v) an inhibitor of lipoxygenase comprising an extract of *Quassia undulata*; (vi) an inhibitor of tyorsinase selected from the group consisting of: an extract of *Quassia undulate*; an extract of *Biophytum petersianum*; an extract of *Allophylus africanus*; and any combination thereof; (vii) an inhibitor of TNF-α selected from the group consisting of: an extract from *Quassia undulate*; an extract of *Allophylus africanus*; an extract of *Canthium dicoccum*; an extract of *Aporosa tetrapleura*; and any combination thereof; (viii) a stimulator of collagen synthesis selected from the group consisting of: *Melanorrhoea laccifera*; an extract of *Canthium dicoccum*; and any combination thereof; and (ix) an inhibitor of B16 melanogenesis comprising an extract from *Quassia undulate*, and (b) a dermatologically acceptable vehicle. In one aspect, the composition comprises an extract from *Quassia undulate* and at least a second extract selected from the group consisting of: *Buchanania reticulate; Melanorrhoea laccifera; Aporosa tetrapleura; Canthium dicoccum*, and any combination thereof. In another aspect, the composition comprises an extract from *Quassia undulate* and *Melanorrhoea laccifera*. In still another aspect, the composition comprises an extract from *Quassia undulata, Buchanania reticulata*, and *Canthium dicoccum*. In even another aspect, the multi-functional topical skin care composition can of claim 2, comprising an extract from *Quassia undulata, Aporosa tetrapleura*, and *Canthium dicoccum*. The extracts can be obtained from all parts of the plant, with the leaf being particularly interesting. The extracts can individually or combinatorially be present in amounts from 0.01% to 20% by weight of said individual extracts or combination of said extracts. The compostion can be formulated in a variety of ways disclosed throughout the specification (e.g., a lotion, cream, gel, serum, emulsion, or powder) The extracts can be alcoholic extracts (e.g., methanol-based extracts). The multi-functional topical skin care composition can further include a moisturizing agent or a humectants and/or at least 40% w/w of water.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, an anti-aging product, a deodorant, an antiperspirant, a perfume, a cologne, etc.

It is also contemplated that compositions of the present invention can be included into food-based products (e.g., beverages, fortified water, energy drinks, nutritional drinks, solid foods, vitamins, supplements, etc.) and pharmaceutical products (e.g., pills, tablets, gel capsules, injectible solutions, drugs, etc.). "Supplements" can include vitamins, minerals, herbs or other botanicals, amino acids, enzymes and metabolites. Such supplements are suitable for oral consumption and can be administered orally.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Pharmaceutically elegant" describes a composition that has particular tactile properties which feel pleasant on the skin (e.g., compositions that are not too watery or greasy, compositions that have a silky texture, compositions that are non-tacky or sticky, etc.). Pharmaceutically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

Description of Illustrative Embodiments

In today's image conscious society, people are continually looking for a product that can improve the visual appearance of their skin. Often times, aged skin, uneven skin tone, or skin damaged by environmental factors such as UV light, chronic sun exposure, environmental pollutants, chemicals, disease pathologies, or smoking, is associated with unattractive skin. Previous attempts to improve the visual appearance of skin has been shown to have various drawbacks such as skin irritation and prolonged recovery periods.

The present invention is an effective alternative to the use of compositions and ingredients currently used to treat aged skin, environmentally-damaged skin, uneven skin tone, and other skin conditions. In one non-limiting embodiment, the compositions of the present invention can be used to treat irritation of the skin and to improve the skin's visual appearance, physiological functions, clinical properties, or biophysical properties by providing a composition of the present invention to an area of the skin that needs such treatment. As noted throughout this specification, the compositions can include any one of an extract from Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha, or Garcinia benthami or any combination thereof or at least 1, 2, 3, 4, 5, 6, 7, 8, 9, 10, 11, 12, 13, 14, 15, 16, 17, 18, 19, 20, 21, 22, or 23 of the extracts in a single composition. These and other non-limiting aspects of the present invention are described in further detail below. Particular combinations of extracts (as identified in the summary of the invention, examples, and claims) can be useful in multi-purpose/multi-benefit skin treatment compositions.

A. Extracts

1. Kunzea ericoides

Kunzea ericoides is considered a shrub or small tree and can produce flowers, fruit, and seeds. It is native to Australia and New Zealand.

The inventors have discovered that extracts of Kunzea ericoides have several biological activities, which can be beneficial to skin. Non-limiting examples of some of these biological activities include inhibiting TNF-α activity and stimulating collagen production in the skin. All of the different portions of Kunzea ericoides can be used to obtain the corresponding extract. Non-limiting examples include its leaves, stems, bark, roots, fruit, flowers or flower buds, kernels, seeds, sap, and the entire plant (i.e., whole plant).

2. Quassia undulata

Quassia undulata is a medium to large sized tree. It has leaves, bark, and can produce flowers and seeds. It is native to western Africa and can be found in Guinea, West Cameroons, Zaire (or Democratic Republic of the Congo), and Angola.

The inventors have discovered that extracts of Quassia undulata have several biological activities, which can be beneficial to skin. Non-limiting examples of some of these biological activities include antioxidant properties and inhibition of COX-1, MMP-1, lipoxygenase, tyrosinase, TNF-α, and B16 melanogenesis activity. All of the different portions of Quassia undulata can be used to obtain the corresponding extract. Non-limiting examples include its leaves, stems, bark, roots, fruit, flowers or flower buds, kernels, seeds, sap, and the entire plant (i.e., whole plant).

3. Diospyros mespiliformis

Diospyros mespiliformis is a large tree that can produce flowers, fruit, and seeds. It is native to Africa and can be located from Ethiopia to south of Swaziland.

The inventors have discovered that extracts of Diospyros mespiliformis have several biological activities, which can be beneficial to skin. Non-limiting examples of some of these biological activities include antioxidant properties, stimulation of collagen production, and inhibition of COX-1, MMP-1, tyrosinase, and TNF-α activity. All of the different portions of Diospyros mespiliformis can be used to obtain the corresponding extract. Non-limiting examples include its leaves, stems, bark, roots, fruit, flowers or flower buds, kernels, seeds, sap, and the entire plant (i.e., whole plant).

4. Khaya senegalensis

Khaya senegalensis is a large tree that can produce flowers, fruit, and seeds. It is native to Africa and can be located in West Africa (e.g., Senegal). It can also be located in Northern Australia.

The inventors have discovered that extracts of Khaya senegalensis have several biological activities, which can be beneficial to skin. Non-limiting examples of some of these biological activities include antioxidant properties, stimulation of collagen production, and inhibition of COX-1, COX-2, MMP-1, and tyrosinase activity. All of the different portions of Khaya senegalensis can be used to obtain the corresponding extract. Non-limiting examples include its leaves, stems, bark, roots, fruit, flowers or flower buds, kernels, seeds, sap, and the entire plant (i.e., whole plant).

5. Biophytum petersianum

Biophytum petersianum is an annual herb that can reach upwards of 40 cm in height. The stem has a hairy appearance with a terminal rosette of pinnate leaves. It typically includes 3-10 pairs of leaflets, decreasing in size with the terminal pair largest and can produce yellow or orange colored flowers. This plant is native to Africa and can be found in Mozambique and Zimbabwe.

The inventors have discovered that extracts of Biophytum petersianum have several biological activities, which can be beneficial to skin. Non-limiting examples of some of these biological activities include antioxidant properties and inhibition of COX-1 and tyrosinase activity. All of the different portions of *Biophytum petersianum* can be used to obtain the corresponding extract. Non-limiting examples include its leaves, stems, bark, roots, fruit, flowers or flower buds, kernels, seeds, sap, and the entire plant (i.e., whole plant).

6. Detarium microcarpum

*Diospyros mespiliformis* is a large tree that can produce flowers, fruit, and seeds. It is native to Africa and can be located from Ethiopia to south of Swaziland.

The inventors have discovered that extracts of *Diospyros mespiliformis* have several biological activities, which can be beneficial to skin. Non-limiting examples of some of these biological activities include antioxidant properties, stimulation of collagen production, and inhibition of COX-1, MMP-1, tyrosinase, TNF-α, and B16 melanogenesis activity. All of the different portions of *Diospyros mespiliformis* can be used to obtain the corresponding extract. Non-limiting examples include its leaves, stems, bark, roots, fruit, flowers or flower buds, kernels, seeds, sap, and the entire plant (i.e., whole plant).

7. *Crossopteryx febrofiga*

*Crossopteryx febrofiga* is considered a shrub or small tree that can produce flowers, fruit, and seeds. It is native to Africa and can be located in tropical African countries.

The inventors have discovered that extracts of *Crossopteryx febrofiga* have several biological activities, which can be beneficial to skin. Non-limiting examples of some of these biological activities include antioxidant properties and inhibition of COX-1, MMP-1, tyrosinase, and TNF-α activity. All of the different portions of *Crossopteryx febrofiga* can be used to obtain the corresponding extract. Non-limiting examples include its leaves, stems, bark, roots, fruit, flowers or flower buds, kernels, seeds, sap, and the entire plant (i.e., whole plant).

8. *Allophylus africanus*

*Allophylus africanus* is considered a shrub or small tree. It has leaves and can produce small creamy-yellow flowers and fruit, which has a red to black color when ripe. This plant is native to Africa and can be found throughout tropical Africa extending to Zimbabwe and South Africa.

The inventors have discovered that extracts of *Allophylus africanus* have several biological activities, which can be beneficial to skin. Non-limiting examples of some of these biological activities include inhibition of COX-1, tyrosinase, and TNF-α activity. All of the different portions of *Allophylus africanus* can be used to obtain the corresponding extract. Non-limiting examples include its leaves, stems, bark, roots, fruit, flowers or flower buds, kernels, seeds, sap, and the entire plant (i.e., whole plant).

9. *Burkea africana*

*Burkea africana* is a medium-sized tree that can produce creamy white flowers, fruit, and seeds. It is native to Tropical Africa and can be found in Chad, Sudan, Tanzania, Uganda, Cameroon, Central African Republic, Zaire, Benin, Burkina Faso, Côte d'Ivoire, Ghana, Guinea, Mali, Niger, Nigeria, Senegal, Togo, Angola, Malawi, Mozambique, Zambia, Zimbabwe, Botswana, Namibia, South Africa in the Transvaal.

The inventors have discovered that extracts of *Burkea africana* have several biological activities, which can be beneficial to skin. Non-limiting examples of some of these biological activities include antioxidant properties and inhibition of COX-1, MMP-1, and tyrosinase activity. All of the different portions of *Burkea africana* can be used to obtain the corresponding extract. Non-limiting examples include its leaves, stems, bark, roots, fruit, flowers or flower buds, kernels, seeds, sap, and the entire plant (i.e., whole plant).

10. *Nauclea latifolia*

*Nauclea latifolia* is considered a shrub or small tree that can produce white flowers, fruit, and seeds. It is native to West Tropical Africa, and can be found in Angola, Cameroon, and Uganda.

The inventors have discovered that extracts of *Nauclea latifolia* have several biological activities, which can be beneficial to skin. Non-limiting examples of some of these biological activities include antioxidant properties, stimulation of collagen production, and inhibition of COX-1 and tyrosinase activity. All of the different portions of *Nauclea latifolia* can be used to obtain the corresponding extract. Non-limiting examples include its leaves, stems, bark, roots, fruit, flowers or flower buds, kernels, seeds, sap, and the entire plant (i.e., whole plant).

11. *Bombax costatum*

*Bombax costatum* is a tree that can produce flowers, fruit, and seeds. It is native to Africa and can be located in Senegal, Guinea, Ghana, Nigeria, and Chad.

The inventors have discovered that extracts of *Bombax costatum* have several biological activities, which can be beneficial to skin. Non-limiting examples of some of these biological activities include antioxidant properties, stimulation of collagen production, and inhibition of COX-1, tyrosinase, and TNF-α activity. All of the different portions of *Bombax costatum* can be used to obtain the corresponding extract. Non-limiting examples include its leaves, stems, bark, roots, fruit, flowers or flower buds, kernels, seeds, sap, and the entire plant (i.e., whole plant).

12. *Buchanania reticulata*

*Buchanania reticulata* is a tree that can produce flowers, fruit, and seeds. It is native to the Pacific, Eastern Indonesia, and the Philippines.

The inventors have discovered that extracts of *Buchanania reticulata* have several biological activities, which can be beneficial to skin. Non-limiting examples of some of these biological activities include antioxidant properties and inhibition of COX-1, COX-2, and MMP-1 activity. All of the different portions of *Buchanania reticulata* can be used to obtain the corresponding extract. Non-limiting examples include its leaves, stems, bark, roots, fruit, flowers or flower buds, kernels, seeds, sap, and the entire plant (i.e., whole plant).

13. *Melanorrhoea laccifera*

*Melanorrhoea laccifera* is a tree. This plant is native to Vietnam.

The inventors have discovered that extracts of *Melanorrhoea laccifera* have several biological activities, which can be beneficial to skin. Non-limiting examples of some of these biological activities include antioxidant properties, stimulation of collagen production, and inhibition of COX-1, COX-2, and MMP-1 activity. All of the different portions of *Melanorrhoea laccifera* can be used to obtain the corresponding extract. Non-limiting examples include its leaves, stems, bark, roots, fruit, flowers or flower buds, kernels, seeds, sap, and the entire plant (i.e., whole plant).

14. *Machilus odoratissimus*

*Machilus odoratissimus* is a tree. This plant is native to the Himalaya's, Singapore, Java, Sumatra, and Cochin China.

The inventors have discovered that extracts of *Machilus odoratissimus* have several biological activities, which can be beneficial to skin. Non-limiting examples of some of these biological activities include inhibition of COX-1, COX-2, MMP-1, and TNF-α activity. All of the different portions of *Machilus odoratissimus* can be used to obtain the corresponding extract. Non-limiting examples include its leaves, stems, bark, roots, fruit, flowers or flower buds, kernels, seeds, sap, and the entire plant (i.e., whole plant).

15. *Spondias pinnata*

*Spondias pinnata* is a tree that can produce flowers, fruit, and seeds. It is native to Tropical Asia and can be found in countries such as Malaysia, Thailand, India, and China.

The inventors have discovered that extracts of *Spondias pinnata* have several biological activities, which can be beneficial to skin. Non-limiting examples of some of these biological activities include antioxidant properties, stimulating collagen production, and inhibition of COX-1 and TNF-α activity. All of the different portions of *Spondias pinnata* can be used to obtain the corresponding extract. Non-limiting examples include its leaves, stems, bark, roots, fruit, flowers or flower buds, kernels, seeds, sap, and the entire plant (i.e., whole plant).

16. *Canthium dicoccum*

*Canthium dicoccum* is a tree that can reach upwards of 12 meters in height. It has leaves and can produce flowers, fruit, and seeds. This plant is native to Malaysia, Nepal, India, and China.

The inventors have discovered that extracts of *Canthium dicoccum* have several biological activities, which can be beneficial to skin. Non-limiting examples of some of these biological activities include stimulating collagen production and inhibition of COX-1 and TNF-α activity. All of the different portions of *Canthium dicoccum* can be used to obtain the corresponding extract. Non-limiting examples include its leaves, stems, bark, roots, fruit, flowers or flower buds, kernels, seeds, sap, and the entire plant (i.e., whole plant).

17. *Parinari annamensis*

*Parinari annamensis* is a tree that can produce flowers, fruit, and seeds. It is native to Vietnam.

The inventors have discovered that extracts of *Parinari annamensis* have several biological activities, which can be beneficial to skin. Non-limiting examples of some of these biological activities include antioxidant properties, stimulating collagen production, and inhibition of MMP-1 activity. All of the different portions of *Parinari annamensis* can be used to obtain the corresponding extract. Non-limiting examples include its leaves, stems, bark, roots, fruit, flowers or flower buds, kernels, seeds, sap, and the entire plant (i.e., whole plant).

18. *Aporosa tetrapleura*

*Aporosa tetrapleura* is a medium sized tree. This plant is native to Vietnam.

The inventors have discovered that extracts of *Aporosa tetrapleura* have several biological activities, which can be beneficial to skin. Non-limiting examples of some of these biological activities include antioxidant properties and inhibition of COX-1, COX-2, MMP-1, and TNF-α activity. All of the different portions of *Aporosa tetrapleura* can be used to obtain the corresponding extract. Non-limiting examples include its leaves, stems, bark, roots, fruit, flowers or flower buds, kernels, seeds, sap, and the entire plant (i.e., whole plant).

19. *Knema globularia*

*Knema globularia* is an evergreen tree that can reach up to 20 meters in height. It can produce flowers, fruit, and seeds. The bark is smooth and has a dark grey-brown color. This plant is native to Burma, Southern China, Malay Peninsula, Indonesia, Thailand, and Laos.

The inventors have discovered that extracts of *Knema globularia* have several biological activities, which can be beneficial to skin. Non-limiting examples of some of these biological activities include antioxidant properties, binding of alpha-2 adrenergic receptor, and inhibition of MMP-1, tyrosinase, and TNF-α activity. All of the different portions of *Knema globularia* can be used to obtain the corresponding extract. Non-limiting examples include its leaves, stems, bark, roots, fruit, flowers or flower buds, kernels, seeds, sap, and the entire plant (i.e., whole plant).

20. *Garcinia gaudichaudii*

*Garcinia gaudichaudii* is a small tree that can produce flowers, fruit, and seeds. It is native to Northern Malaysia.

The inventors have discovered that extracts of *Garcinia gaudichaudii* have several biological activities, which can be beneficial to skin. Non-limiting examples of some of these biological activities include antioxidant properties, binding of alpha-2 adrenergic receptor, and inhibition of COX-2 and TNF-α activity. All of the different portions of *Garcinia gaudichaudii* can be used to obtain the corresponding extract. Non-limiting examples include its leaves, stems, bark, roots, fruit, flowers or flower buds, kernels, seeds, sap, and the entire plant (i.e., whole plant).

21. *Randia dasycarpa*

*Randia dasycarpa* is a tree that can produce flowers, fruit, and seeds. It is native to Thailand.

The inventors have discovered that extracts of *Randia dasycarpa* have several biological activities, which can be beneficial to skin. Non-limiting examples of some of these biological activities include binding of alpha-2 adrenergic receptor and inhibition of MMP-1 activity. All of the different portions of *Randia dasycarpa* can be used to obtain the corresponding extract. Non-limiting examples include its leaves, stems, bark, roots, fruit, flowers or flower buds, kernels, seeds, sap, and the entire plant (i.e., whole plant).

22. *Capparis micrantha*

*Capparis micrantha* is a shrub or tree that can produce flowers, fruit, and seeds. It is native to the Philippines.

The inventors have discovered that extracts of *Capparis micrantha* have several biological activities, which can be beneficial to skin. Non-limiting examples of some of these biological activities include antioxidant properties, stimulating collagen production, and inhibition of COX-1, and lipoxygenase activity. All of the different portions of *Capparis micrantha* can be used to obtain the corresponding extract. Non-limiting examples include its leaves, stems, bark, roots, fruit, flowers or flower buds, kernels, seeds, sap, and the entire plant (i.e., whole plant).

23. *Garcinia benthami*

*Garcinia benthami* is tree that can reach up to 18 meters in height. It can produce flowers, fruit, and seeds. It is native to India and Sri Lanka.

The inventors have discovered that extracts of *Garcinia benthami* have several biological activities, which can be beneficial to skin. Non-limiting examples of some of these biological activities include antioxidant properties, stimulating collagen production, and inhibition of COX-1, MMP-1, lipoxygenase, and TNF-α activity. All of the different portions of *Garcinia benthami* can be used to obtain the corresponding extract. Non-limiting examples include its leaves, stems, bark, roots, fruit, flowers or flower buds, kernels, seeds, sap, and the entire plant (i.e., whole plant).

24. Extraction Methods

A person of ordinary skill in the art would be able to isolate any one of the extracts identified above from parts of the corresponding plant by using any suitable method known in the art. In one non-limiting example, the plant (or any part of the plant such as the leaves, stems, bark, roots, fruit, flowers or flower buds, fruit, seeds, seed pods, sap, whole plant, etc.) can be disrupted by mechanical means which results in a puree. The puree is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant extract can then be used in the compositions of the present invention.

In other aspects, aqueous, alcoholic, or oil based extraction techniques, or combinations thereof, can be used on the whole plant or any part thereof of (e.g., leaves, stems, bark, roots, fruit, flowers or flower buds, fruit, seeds, seed pods, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), etc.

Additional extraction processes used by the inventors are described in the Examples.

B. Compositions of the Present Invention

1. Combinations and Amounts of Ingredients

It is contemplated that the compositions of the present invention can include an extract of *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha,* or *Garcinia benthami* or any combination thereof or at least 1, 2, 3, 4, 5, 6, 7, 8, 9, 10, 11, 12, 13, 14, 15, 16, 17, 18, 19, 20, 21, 22, or 23 of such extracts. The compositions can also include additional ingredients described throughout this specification. The concentrations of the plant extracts and/or additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the plant extracts identified in this specification or any combination thereof or additional ingredients. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, pastes, milks, liquids, aerosols, solid forms, or eye jellies. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product.

It is also contemplated that the plant extracts and additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. Nos. 6,387,398; 6,203,802; 5,411,744; Kreuter 1988).

Also contemplated are pharmaceutically-acceptable or pharmacologically-acceptable compositions. The phrase "pharmaceutically-acceptable" or "pharmacologically-acceptable" includes compositions that do not produce an allergic or similar untoward reaction when administered to a human. Typically, such compositions are prepared either as topical compositions, liquid solutions or suspensions, solid forms suitable for solution in, or suspension in, liquid prior to use can also be prepared. Routes of administration can vary with the location and nature of the condition to be treated, and include, e.g., topical, inhalation, intradermal, transdermal, parenteral, intravenous, intramuscular, intranasal, subcutaneous, percutaneous, intratracheal, intraperitoneal, intratumoral, perfusion, lavage, direct injection (e.g., an injectable solution), and oral administration and formulation (e.g., tablets, capsules, etc.).

3. Products

The compositions of the present invention can be incorporated into products. Non-limiting examples of products include cosmetic products, food-based products (e.g., fortified water, energy drinks, nutritional drinks, vitamins, supplements, solid foods), pharmaceutical products, etc. By way of example only, non-limiting cosmetic products include sunscreen products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products. Further products can include hair re-growth compositions, serums, sprays, and the like.

4. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA International Cosmetic Ingredient Dictionary and Handbook (2008), $12^{th}$ Edition, describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) water-proofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Sunscreen Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 56, 7, 8, 9, 10, 11, 12, 13, 14, 15, 20, 25, 30, 35, 40, 45, 50, 55, 60, 70, 80, 90 or more, or any integer or derivative therein.

ii. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea officinalis extract, aluminum starch octenylsuccinate, aluminum stearate, apricot (*Prunus armeniaca*) kernel oil, arginine, arginine aspartate, arnica montana extract, ascorbic acid, ascorbyl palmitate, aspartic acid, avocado (*Persea gratissima*) oil, barium sulfate, barrier sphingolipids, butyl alcohol, beeswax, behenyl alcohol, beta-sitosterol, BHT, birch (*Betula alba*) bark extract, borage (*Borago officinalis*) extract, 2-bromo-2-nitropropane-1,3-diol, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrageenan (*Chondrus crispus*), carrot (*Daucus carota* sativa) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*)oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*Oenothera biennis*) oil, fatty acids, tructose, gelatin, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, honey, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (citrus *Medica limonum*) oil, linoleic acid, linolenic acid, *Macadamia ternifolia* nut oil, magnesium stearate, magnesium sulfate, maltitol, matricaria (*Chamomilla recutita*) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (citrus *Aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, salicylic acid, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (prunus *Amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

iii. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

iv. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

v. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

vi. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, poly silicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

vii. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

viii. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

C. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Materials and Methods for Obtaining Extracts

But for *Kunzea ericoides* leaf extract, all of the remaining extracts listed in Tables 1-6 were prepared by first crushing the plant part (e.g., leaf, root, or bark) followed by drying. The dried plant material was then washed with heptane, followed by washing with ethyl acetate. The washed material was then extracted with 100% methanol. The extract was then collected and subjected to the assays described below.

For *Kunzea ericoides* leaf extract, leafs were collected and dried. The dried leafs were then milled and then extracted with water. The aqueous liquid was collected, preservatives were added, and the liquid was stored in a 50/50 solution of butylene glycol and denatured alcohol.

Each extract in Table 1 was prepared by and provided to the inventors by Southern Cross Botanicals Pty. Ltd., New South Wales, Australia.

Example 2

Efficacy of Extracts

Each extract prepared according to the processes described in Example 1 was subjected to a variety of assays to determine their skin efficacy. The following Tables 1-6 provide a summary of these data. A description of the assays used to obtain these data is provided below Table 6. Tables 2-6 provide particular combinations of extracts shown to have multi-beneficial properties for skin.

TABLE 1*

| Extract** | COX-1 Inhib. | COX-2 Inhib. | AO Activity | MMP-1 Inhib. | LO Inhib. | Tyrosinase Inhib. | TNF-α Inhib. | Collagen Simulated | B16 Inhib. | Binding Alpha-2 Adrenergic Receptor |
|---|---|---|---|---|---|---|---|---|---|---|
| *Quassia undulata* leaf | Yes | — | Yes | Yes | Yes | Yes | Yes | — | Yes | — |
| *Biophytum petersianum* leaf | Yes | — | Yes | — | — | Yes | — | — | — | — |
| *Allophylus africanus* leaf | Yes | — | — | — | — | Yes | Yes | — | — | — |
| *Buchanania reticulata* leaf | Yes | Yes | Yes | Yes | — | — | — | — | — | — |
| *Melanorrhoea laccifera* leaf | Yes | Yes | Yes | Yes | — | — | — | Yes | — | — |
| *Canthium dicoccum* leaf | Yes | — | — | — | — | — | Yes | Yes | — | — |
| *Aporosa tetrapleura* leaf | Yes | Yes | Yes | Yes | — | — | Yes | — | — | — |
| *Detarium microcarpum* root | Yes | — | Yes | Yes | — | Yes | Yes | Yes | Yes | — |
| *Burkea africana* bark | Yes | — | Yes | Yes | — | Yes | — | — | — | — |
| *Nauclea latifolia* root | Yes | — | Yes | — | — | Yes | — | Yes | — | — |
| *Spondias pinnata* leaf | Yes | — | Yes | — | — | — | Yes | Yes | — | — |
| *Parinari annamensis* leaf | — | — | Yes | Yes | — | — | — | Yes | — | — |
| *Randia dasycarpa* leaf | — | — | — | Yes | — | — | — | — | — | Yes |
| *Capparis micrantha* leaf | Yes | — | Yes | — | Yes | — | — | Yes | — | — |
| *Kunzea ericoides* leaf | — | — | — | — | — | — | Yes | Yes | — | — |
| *Diospyros mespiliformis* leaf | Yes | — | Yes | Yes | — | Yes | Yes | Yes | — | — |
| *Khaya senegalensis* bark | Yes | Yes | Yes | Yes | — | Yes | — | Yes | — | — |
| *Crossopteryx febrofiga* leaf | Yes | — | Yes | Yes | — | Yes | Yes | — | — | — |
| *Bombax costatum* leaf | Yes | — | Yes | — | — | Yes | Yes | Yes | — | — |
| *Knema globularia* leaf | — | — | Yes | Yes | — | Yes | Yes | — | — | Yes |
| *Garcinia gaudichaudii* leaf | — | Yes | Yes | — | — | — | Yes | — | — | Yes |
| *Garcinia benthami* leaf | Yes | — | Yes | Yes | Yes | — | Yes | Yes | — | — |

TABLE 1*-continued

| Extract** | COX-1 Inhib. | COX-2 Inhib. | AO Activity | MMP-1 Inhib. | LO Inhib. | Tyrosinase Inhib. | TNF-α Inhib. | Collagen Simulated | B16 Inhib. | Binding Alpha-2 Adrenergic Receptor |
|---|---|---|---|---|---|---|---|---|---|---|
| Machilus odoratissimus leaf | Yes | Yes | — | Yes | — | — | Yes | | | |

*Inhib. = Inhibition. AO = Antioxidant. LO = Lipoxygenase. B16 = B16 Melanogenesis. Collagen Stimulated = collagen production stimulated.
**Yes means that the extract provided a level of inhibition, antioxidant activity, increased collagen production, and/or binding of alpha-2 adrenergic receptor to be efficacious in treating skin conditions associated with such enzymes, proteins, binding sites, and antioxidants.

TABLE 2*

| Extract** | COX-1 Inhib. | COX-2 Inhib. | AO Activity | MMP-1 Inhib. | LO Inhib. | Tyrosinase Inhib. | TNF-α Inhib. | Collagen Simulated | B16 Inhib. |
|---|---|---|---|---|---|---|---|---|---|
| Quassia undulata leaf | Yes | — | Yes | Yes | Yes | Yes | Yes | — | Yes |
| Melanorrhoea laccifera leaf | Yes | Yes | Yes | Yes | — | — | — | Yes | — |

*Inhib. = Inhibition. AO = Antioxidant. LO = Lipoxygenase. B16 = B16 Melanogenesis. Collagen Stimulated = collagen production stimulated.
**Yes means that the extract provided a level of inhibition, antioxidant activity, increased collagen production, and/or binding of alpha-2 adrenergic receptor to be efficacious in treating skin conditions associated with such enzymes, proteins, binding sites, and antioxidants.

The combination in Table 2 was shown to have a broad range of skin benefits, which makes such combination useful as a multi-purpose/multi-functional skin treatment composition.

TABLE 3*

| Extract** | COX-1 Inhib. | COX-2 Inhib. | AO Activity | MMP-1 Inhib. | LO Inhib. | Tyrosinase Inhib. | TNF-α Inhib. | Collagen Simulated | B16 Inhib. |
|---|---|---|---|---|---|---|---|---|---|
| Quassia undulata leaf | Yes | — | Yes | Yes | Yes | Yes | Yes | — | Yes |
| Buchanania reticulata leaf | Yes | Yes | Yes | Yes | — | — | — | — | — |
| Canthium dicoccum leaf | Yes | — | — | — | — | — | Yes | Yes | — |

*Inhib. = Inhibition. AO = Antioxidant. LO = Lipoxygenase. B16 = B16 Melanogenesis. Collagen Stimulated = collagen production stimulated.
**Yes means that the extract provided a level of inhibition, antioxidant activity, increased collagen production, and/or binding of alpha-2 adrenergic receptor to be efficacious in treating skin conditions associated with such enzymes, proteins, binding sites, and antioxidants.

The combination in Table 3 was shown to have a broad range of skin benefits, which makes such combination useful as a multi-purpose/multi-functional skin treatment composition.

TABLE 4*

| Extract** | COX-1 Inhib. | COX-2 Inhib. | AO Activity | MMP-1 Inhib. | LO Inhib. | Tyrosinase Inhib. | TNF-α Inhib. | Collagen Simulated | B16 Inhib. |
|---|---|---|---|---|---|---|---|---|---|
| Quassia undulata leaf | Yes | — | Yes | Yes | Yes | Yes | Yes | — | Yes |
| Canthium dicoccum leaf | Yes | — | — | — | — | — | Yes | Yes | — |

TABLE 4*-continued

| Extract** | COX-1 Inhib. | COX-2 Inhib. | AO Activity | MMP-1 Inhib. | LO Inhib. | Tyrosinase Inhib. | TNF-α Inhib. | Collagen Simulated | B16 Inhib. |
|---|---|---|---|---|---|---|---|---|---|
| Aporosa tetrapleura leaf | Yes | Yes | Yes | Yes | — | — | Yes | — | — |

*Inhib. = Inhibition. AO = Antioxidant. LO = Lipoxygenase. B16 = B16 Melanogenesis. Collagen Stimulated = collagen production stimulated.
**Yes means that the extract provided a level of inhibition, antioxidant activity, increased collagen production, and/or binding of alpha-2 adrenergic receptor to be efficacious in treating skin conditions associated with such enzymes, proteins, binding sites, and antioxidants.

The combination in Table 4 was shown to have a broad range of skin benefits, which makes such combination useful as a multi-purpose/multi-functional skin treatment composition.

TABLE 5*

| Extract** | COX-1 Inhib. | COX-2 Inhib. | AO Activity | MMP-1 Inhib. | LO Inhib. | Tyrosinase Inhib. | TNF-α Inhib. | Collagen Simulated | B16 Inhib. | Binding Alpha-2 Adrenergic Receptor |
|---|---|---|---|---|---|---|---|---|---|---|
| Quassia undulata leaf | Yes | — | Yes | Yes | Yes | Yes | Yes | — | Yes | — |
| Kunzea ericoides leaf | — | — | — | — | — | — | Yes | Yes | — | — |
| Garcinia gaudichaudii leaf | — | Yes | Yes | — | — | — | Yes | — | — | Yes |

*Inhib. = Inhibition. AO = Antioxidant. LO = Lipoxygenase. B16 = B16 Melanogenesis. Collagen Stimulated = collagen production stimulated.
**Yes means that the extract provided a level of inhibition, antioxidant activity, increased collagen production, and/or binding of alpha-2 adrenergic receptor to be efficacious in treating skin conditions associated with such enzymes, proteins, binding sites, and antioxidants.

The combination in Table 5 was shown to have a broad range of skin benefits, which makes such combination useful as a multi-purpose/multi-functional skin treatment composition.

TABLE 6*

| Extract** | COX-1 Inhib. | COX-2 Inhib. | AO Activity | MMP-1 Inhib. | LO Inhib. | Tyrosinase Inhib. | TNF-α Inhib. | Collagen Simulated | B16 Inhib. | Binding Alpha-2 Adrenergic Receptor |
|---|---|---|---|---|---|---|---|---|---|---|
| Quassia undulata leaf | Yes | — | Yes | Yes | Yes | Yes | Yes | — | Yes | — |
| Buchanania reticulata leaf | Yes | Yes | Yes | Yes | — | — | — | — | — | — |
| Canthium dicoccum leaf | Yes | — | — | — | — | — | Yes | Yes | — | — |
| Randia dasycarpa leaf | — | — | — | Yes | — | — | — | — | — | Yes |

*Inhib. = Inhibition. AO = Antioxidant. LO = Lipoxygenase. B16 = B16 Melanogenesis. Collagen Stimulated = collagen production stimulated.
**Yes means that the extract provided a level of inhibition, antioxidant activity, increased collagen production, and/or binding of alpha-2 adrenergic receptor to be efficacious in treating skin conditions associated with such enzymes, proteins, binding sites, and antioxidants.

The combination in Table 6 was shown to have a broad range of skin benefits, which makes such combination useful as a multi-purpose/multi-functional skin treatment composition Antioxidant (AO) assay: An in vitro bioassay that measures the total anti-oxidant capacity of an extract. The assay relies on the ability of antioxidants in the sample to inhibit the oxidation of ABTS® (2,2'-azino-di-[3-ethylbenzthiazoline sulphonate]) to ABTS®.+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents.

Anti-Oxidant capacity kit #709001 from Cayman Chemical (Ann Arbor, Mich. USA) was used as an in vitro bioassay to measure the total anti-oxidant capacity of each of the extracts identified in Table 1. The protocol was followed according to manufacturer recommendations. The assay relied on antioxidants in the sample to inhibit the oxidation of ABTS® (2,2'-azino-di-[3-ethylbenzthiazoline sulphonate]) to ABTS®.+ by metmyoglobin. The capacity of the antioxidants in the sample to prevent ABTS oxidation was compared with that Trolox, a water-soluble tocopherol analogue, and was quantified as a molar Trolox equivalent.

Tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes.

Purified mushroom tyrosinase (Sigma) was incubated with its substrate L-Dopa (Fisher) in the presence or absence of each of the extracts in Table 1. Pigment formation was evaluated by colorimetric plate reading at 490 nm. The percent inhibition of mushroom tyrosinase activity was calculated compared to non-treated controls to determine the ability of test extracts to inhibit the activity of purified enzyme. Test extract inhibition was compared with that of kojic acid (Sigma).

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay analyzes the effect of extracts on the production of TNF-α by human epidermal keratinocytes. The endpoint of this assay is a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples are pipetted into the wells and any TNF-α ☐present is bound by the immobilized antibody. After washing away any unbound substances, an enzyme-linked polyclonal antibody specific for TNF-α is added to the wells. Following a wash to remove any unbound antibody-enzyme reagent, a substrate solution is added to the wells and color develops in proportion to the amount of TNF-α bound in the initial step using a microplate reader for detection at 450 nm. The color development is stopped and the intensity of the color is measured.

Subconfluent normal human adult keratinocytes (Cascade Biologics) cultivated in EpiLife standard growth medium (Cascade Biologics) at 37° C. in 5% $CO_2$, were treated with phorbol 12-myristate 13-acetate (PMA, 10 ng/ml, Sigma Chemical, #P1585-1MG) and each of the extracts identified in Table 1 for 6 hours. PMA has been shown to cause a dramatic increase in TNF-α secretion which peaks at 6 hours after treatment. Following incubation, cell culture medium was collected and the amount of TNF-α secretion quantified using a sandwhich enzyme linked immuno-sorbant assay (ELISA) from R&D Systems (#DTA00C).

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid.

The Colorimetric LO Inhibitor screening kit (#760700, Cayman Chemical) was used to determine the ability of each of the extracts identified in Table 1 to inhibit enzyme activity. Purified 15-lipoxygenase and test extracts were mixed in assay buffer and incubated with shaking for 10 min at room temperature. Following incubation, arachidonic acid was added to initiate the reaction and mixtures incubated for an additional 10 min at room temperature. Colorimetric substrate was added to terminate catalysis and color progression was evaluated by fluorescence plate reading at 490 nm. The percent inhibition of lipoyganse activity was calculated compared to non-treated controls to determine the ability of test extracts to inhibit the activity of purified enzyme.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors.

The Colormetric COX (ovine) Inhibitor screening assay (#760111, Cayman Chemical), was used to analyze the effects of each of the extracts identified in Table 1 on the activity of purified clooxygnase enzyme (COX-1 or COX-2). According to manufacturer instructions, purified enzyme, heme and test extracts were mixed in assay buffer and incubated with shaking for 15 min at room temperature. Following incubation, arachidonic acid and colorimetric substrate were added to initiate the reaction. Color progression was evaluated by colorimetric plate reading at 590 nm. The percent inhibition of COX-1 or COX-2 activity was calculated compared to non-treated controls to determine the ability of test extracts to inhibit the activity of purified enzyme.

Matrix Metalloproteinase Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen was used as an in vitro assay to measure MMP1 enzymatic activity for each of the extracts identified in Table 1. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Binding of Alpha-2 Adrenergic Receptor Assay: This assay provides data on the binding affinity ($K_D$) and receptor numbers that have been bound ($B_{max}$) for the extracts identified in Table 1. Binding of this receptor produces vasoconstrictive properties in blood vessels. Therefore, an alpha-2 adrenergic receptor agonist can be effective in treating erythemic skin, rosacea, inflamed skin, actinic purpura, peri-procedureal bruising of the skin, etc.

Human HT29 cells were used as the receptor source. [$^3$H]MK-912 (60-80 Ci/mmol) was used as the radioligand, with a final concentration of 0.75 nM. The referenced compound was oxymetazoline. The non-specific determinant was L(−)-Norepinephrine at a concentration of 100 uM. The positive control was rauwolscine. The incubation conditions were carried out in 50 nm TRIS-HC1 (pH 7.5) at 25° C. for 60 minutes. The reaction is terminated by rapid vacuum filtration onto glass fiber filters. Radioactivity trapped onto the filters is determined and compared to control values in order to ascertain any interactions of the test compound (extract) with the alpha$_{2A}$ adrenergic binding site. Results are provided in Table 1. References explaining this assay in further detail include (1) Bylund et al., Alpha-2A and 2B Adrenergic Receptor Subtypes: Antagonist Binding in Tissues and Cell Lines Containing Only One Subtype, *J. Pharmac. & Exp. Ther.* 245(2): 600-607 (1988) and (2) Totaro et al., [$^3$H]L-657, 743 (MK-912): A New, High Affinity Selective Radioligand for Brain Alpha-2 Adrenoceptors, *Life Sciences* 44:459-467 (1989), both of which are incorporated by reference.

Collagen Stimulation Assay: Collagen is an extracellular matrix protein critical for skin structure. Increased synthesis of collagen helps improve skin firmness and elasticity. This bioassay analyzes the effect of extracts on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples are pipetted into the wells and any procollagen peptide □present is bound by the immobilized antibody. After washing away any unbound substances, an enzyme-linked polyclonal antibody specific for procollagen peptide is added to the wells. Following a wash to remove any unbound antibody-enzyme reagent, a substrate solution is added to the wells and color develops in proportion to the amount of procollagen peptide bound in the initial step using a microplate reader for detection at 450 nm. The color development is stopped and the intensity of the color is measured.

Subconfluent normal human adult epidermal fibroblasts (Cascade Biologics) cultivated in standard DMEM growth medium with 10% fetal bovine serum (Mediatech) at 37° C. in 10% $CO_2$, were treated with each of the extracts identified in Table 1 for 3 days. Following incubation, cell culture medium was collected and the amount of procollagen peptide secretion quantified using a sandwhich enzyme linked immuno-sorbant assay (ELISA) from Takara (#MK101).

B16 Melanogenesis Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, cultivated in standard DMEM growth medium with 10% fetal bovine serum (Mediatech) at 37° C. in 10% $CO_2$, were treated with each of the extracts identified in Table 1 for 6 days. Following incubation, melanin secretion was measured by absorbance at 405 nm and cellular viability was quantified.

Example 3

Testing Vehicles and Sample Compositions

Tables 7 and 8 describe generic skin testing formulations in which a skin active ingredient can be incorporated into to determine the types of skin benefits that can be attributed to the skin active ingredient. These formulations are prepared in such a manner that any resulting skin benefit from topical application of the formula to skin can be directly attributed to the skin active ingredient being tested. In the context of the present invention, the skin active ingredient that can be tested can be an extract from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha,* or *Garcinia benthami* or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant extract can be used for testing (e.g., root, stem, leaf, flower, flower bulb, bark, fruit, seed, sap, whole plant etc.). In particular aspects, the combinations of skin actives identified in any one of Tables 2-6 are particularly interesting for use in multi-functional/multi-beneficial skin treatment compositions. It should be recognized that other standard testing vehicles can also be used to determine the skin benefit properties of extracts obtained from the plant extracts and that the following formulations are non-limiting testing vehicles.

TABLE 7*

| Ingredient | % Concentration (by weight) |
|---|---|
| Phase A | |
| Water | 84.80 |
| Xanthum gum | 0.1 |
| M-paraben | 0.15 |

TABLE 7*-continued

| Ingredient | % Concentration (by weight) |
|---|---|
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C** | |
| Skin Active Ingredient | 2.0 |
| TOTAL | 100 |

*Procedure for making composition: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. In particular embodiments, the extracts can be an extract from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha,* or *Garcinia benthami,* or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant can be used to create the skin-active extract (e.g., root, stem, leaf, flower, flower bulb, bark, fruit, seed, seed pod, sap whole plant etc.). In particular aspects, the combinations of skin actives identified in any one of Tables 2-6 are particularly interesting for use in multi-functional/multi-beneficial skin treatment compositions.

TABLE 8*

| Ingredient | % Concentration (by weight) |
|---|---|
| Phase A | |
| Water | 78.6 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C** | |
| Skin Active Ingredient | 2.0 |
| TOTAL | 100 |

*Add ingredients in phase A to beaker and heat to 70-75° C. while mixing. Subsequently, add the phase B ingredient with phase A and cool to 30° C. with mixing. Subsequently, add phase C ingredient while mixing.
**The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. In particular embodiments, the extracts can be an extract from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha,* or *Garcinia benthami,* or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant can be used to create the skin-active extract (e.g., root, stem, leaf, flower, flower bulb, bark, fruit, seed, seed pod, sap whole plant etc.). In particular aspects, the combinations of skin actives identified in any one of Tables 2-6 are particularly interesting for use in multi-functional/multi-beneficial skin treatment compositions The formulations represented in Table 9-14 are non-limiting examples of the types of formulations that can be prepared in the context of the present invention. Any standard method can be used to prepare such formulations. For instance, simple mixing of the ingredients in a beaker can be used. One should mix such ingredients and add heat as necessary to obtain a homogenous composition.

Table 9 includes a non-limiting example of a composition of the present invention. The composition can be formulated into an emulsion (e.g., o/w, w/o, o/w/o, w/o/w, etc.) and the additional ingredients identified throughout the specification can be included into the Table 9 composition (e.g., by adjusting the water content of composition). Further, the concentration ranges of the ingredients identified in Table 9 can vary depending on a desired formulation (e.g., cream, lotion, moisturizer cleanser, etc.).

TABLE 9

| Ingredient | % Concentration (by weight) |
|---|---|
| Water | q.s. |
| Skin active ingredient* | 0.1% to 10% |
| Glycerin | 3 to 40% |
| Butylene glycol | 0.0001 to 10% |
| Propylene glycol | 0.0001 to 10% |
| Phenoxyethanol | 0.0001 to 10% |
| Disodium EDTA | 0.0001 to 10% |
| Steareth-20 | 0.0001 to 10% |
| Chlorhexidine Diglunonate | 0.0001 to 10% |
| Potassium Sorbate | 0.0001 to 10% |
| Preservative** | 0.0001 to 2% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. In particular embodiments, the extracts can be an extract from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha,* or *Garcinia benthami,* or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant can be used to create the skin-active extract (e.g., root, stem, leaf, flower, flower bulb, bark, fruit, seed, seed pod, sap whole plant etc.). In particular aspects, the combinations of skin actives identified in any one of Tables 2-6 are particularly interesting for use in multi-functional/multi-beneficial skin treatment compositions.
**Any preservative can be used identified in the specification or those known in the art.

Table 10 includes a non-limiting example of a composition of the present invention. The composition can be formulated into an emulsion (e.g., o/w, w/o, o/w/o, w/o/w, etc.) and the additional ingredients identified throughout the specification can be included into the Table 10 composition (e.g., by adjusting the water content of composition). Further, the concentration ranges of the ingredients identified in Table 10 can vary depending on a desired formulation (e.g., cream, lotion, moisturizer cleanser, etc.).

TABLE 10

| Ingredient | % Concentration (by weight) |
|---|---|
| Water | q.s. |
| Skin active ingredient* | 0.1% to 10% |
| Dimethicone | 0.0001 to 10% |
| Triethanolamine | 0.0001 to 10% |
| Phenonip | 0.0001 to 10% |
| Betaine | 0.0001 to 10% |
| Disodium EDTA | 0.0001 to 10% |
| Tocopheryl acetate | 0.0001 to 10% |

TABLE 10-continued

| Ingredient | % Concentration (by weight) |
|---|---|
| Prodew 400 | 0.0001 to 10% |
| Preservative** | 0.0001 to 2% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. In particular embodiments, the extracts can be an extract from Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha, or Garcinia benthami, or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant can be used to create the skin-active extract (e.g., root, stem, leaf, flower, flower bulb, bark, fruit, seed, seed pod, sap whole plant etc.). In particular aspects, the combinations of skin actives identified in any one of Tables 2-6 are particularly interesting for use in multi-functional/multi-beneficial skin treatment compositions.
**Any preservative can be used identified in the specification or those known in the art.

Table 11 includes a non-limiting example of a composition of the present invention. The composition can be formulated into an emulsion (e.g., o/w, w/o, o/w/o, w/o/w, etc.) and the additional ingredients identified throughout the specification can be included into the Table 11 composition (e.g., by adjusting the water content of composition). Further, the concentration ranges of the ingredients identified in Table 11 can vary depending on a desired formulation (e.g., cream, lotion, moisturizer cleanser, etc.). In particular embodiments, the Table 11 composition can be a moisturizer.

TABLE 11

| Ingredient | % Concentration (by weight) |
|---|---|
| Water | q.s. |
| Skin active ingredient* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Capric/Caprylic Triglyceride | 0.0001 to 10% |
| Lipex 205 (Shea Butter) | 0.0001 to 10% |
| Squalane | 0.0001 to 10% |
| Cetyl Alcohol | 0.0001 to 10% |
| Dimethicone | 0.0001 to 10% |
| Ceramide II | 0.0001 to 10% |
| Stearic Acid | 0.0001 to 10% |
| Super Sterol Ester | 0.0001 to 10% |
| Arlacel 165 | 0.0001 to 10% |
| Simulgel 600 | 0.0001 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. In particular embodiments, the extracts can be an extract from Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha, or Garcinia benthami, or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant can be used to create the skin-active extract (e.g., root, stem, leaf, flower, flower bulb, bark, fruit, seed, seed pod, sap whole plant etc.). In particular aspects, the combinations of skin actives identified in any one of Tables 2-6 are particularly interesting for use in multi-functional/multi-beneficial skin treatment compositions.

Table 12 includes a non-limiting example of a composition of the present invention. The composition can be formulated into an emulsion (e.g., o/w, w/o, o/w/o, w/o/w, etc.) and the additional ingredients identified throughout the specification can be included into the Table 12 composition (e.g., by adjusting the water content of composition). Further, the concentration ranges of the ingredients identified in Table 12 can vary depending on a desired formulation (e.g., cream, lotion, moisturizer cleanser, etc.). In particular embodiments, the Table 12 composition can be a moisturizer.

TABLE 12

| Ingredient | % Concentration (by weight) |
|---|---|
| Water | q.s. |
| Skin active ingredient* | 0.1% to 10% |
| Glycerin | 0.0001 to 10% |
| Pentylene Glycol | 0.0001 to 10% |
| Capryl Glycol | 0.0001 to 10% |
| Disodium EDTA | 0.0001 to 10% |
| Petrolatum | 0.0001 to 10% |
| Squalane | 0.0001 to 10% |
| Cetyl Alcohol | 0.0001 to 10% |
| Arlacel 165 | 0.0001 to 10% |
| Dimethicone | 0.0001 to 10% |
| Simulgel 600 | 0.0001 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. In particular embodiments, the extracts can be an extract from Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha, or Garcinia benthami, or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant can be used to create the skin-active extract (e.g., root, stem, leaf, flower, flower bulb, bark, fruit, seed, seed pod, sap whole plant etc.). In particular aspects, the combinations of skin actives identified in any one of Tables 2-6 are particularly interesting for use in multi-functional/multi-beneficial skin treatment compositions.

Table 13 includes a non-limiting example of a composition of the present invention. The composition can be formulated into an emulsion (e.g., o/w, w/o, o/w/o, w/o/w, etc.) and the additional ingredients identified throughout the specification can be included into the Table 13 composition (e.g., by adjusting the water content of composition). Further, the concentration ranges of the ingredients identified in Table 13 can vary depending on a desired formulation (e.g., cream, lotion, moisturizer cleanser, etc.). In particular embodiments, the Table 13 composition can be a sunscreen lotion.

TABLE 13

| Ingredient | % Concentration (by weight) |
|---|---|
| Water | q.s. |
| Skin active ingredient* | 0.1% to 10% |
| Xanthan Gum | 0.0001 to 10% |
| Disodium EDTA | 0.0001 to 10% |
| Pentylene Glycol | 0.0001 to 10% |
| Capryl Glycol | 0.0001 to 10% |
| Pemulen TR-1 | 0.0001 to 10% |
| Triethanolamine | 0.0001 to 10% |
| PVP/Hexadecene Copolymer | 0.0001 to 10% |

TABLE 13-continued

| Ingredient | % Concentration (by weight) |
| --- | --- |
| Finsolv TN | 10 to 30% |
| Sorbitan Isostearate | 0.0001 to 10% |
| Sunscreen Ingredient** | 2 to 25% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. In particular embodiments, the extracts can be an extract from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha*, or *Garcinia benthami*, or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant can be used to create the skin-active extract (e.g., root, stem, leaf, flower, flower bulb, bark, fruit, seed, seed pod, sap whole plant etc.). In particular aspects, the combinations of skin actives identified in any one of Tables 2-6 are particularly interesting for use in multi-functional/multi-beneficial skin treatment compositions.

Table 14 includes a non-limiting example of a composition of the present invention. The additional ingredients identified throughout the specification can be included into the Table 14 composition (e.g., by adjusting the water content of composition). Further, the concentration ranges of the ingredients identified in Table 14 can vary depending on a desired formulation (e.g., cream, lotion, moisturizer cleanser, etc.). In particular embodiments, the Table 14 composition can be a cleanser.

TABLE 14

| Ingredient | % Concentration (by weight) |
| --- | --- |
| Water | q.s. |
| Skin active ingredient* | 0.1% to 10% |
| Disodium EDTA | 0.0001 to 10% |
| Citric Acid | 0.0001 to 10% |
| Pentylene Glycol | 0.0001 to 10% |
| Capryl Glycol | 0.0001 to 10% |
| sodium methyl cocoyl taurate | 10 to 30% |
| sodium cocoamphodiacetate | 1 to 10% |
| TOTAL | 100 |

*The plant extracts identified throughout this specification can be incorporated into this testing formulation as the skin active ingredient. The extracts can be individually used or combined in this testing vehicle. The concentration ranges of the extract (or combination of extracts) can be modified as desired or needed by increasing or decreasing the amount of water. In particular embodiments, the extracts can be an extract from *Kunzea ericoides, Quassia undulata, Diospyros mespiliformis, Khaya senegalensis, Biophytum petersianum, Detarium microcarpum, Crossopteryx febrofiga, Allophylus africanus, Burkea africana, Nauclea latifolia, Bombax costatum, Buchanania reticulata, Melanorrhoea laccifera, Machilus odoratissimus, Spondias pinnata, Canthium dicoccum, Parinari annamensis, Aporosa tetrapleura, Knema globularia, Garcinia gaudichaudii, Randia dasycarpa, Capparis micrantha*, or *Garcinia benthami*, or any combination thereof, or at least 1, 2, 3, 4, 5, 6, 7, 8, 9, 10, 11, 12, 13, 14, 15, 16, 17, 18, 19, 20, 21, 22, or 23 of said extracts in a single composition. Any portion of the plant can be used to create the skin-active extract (e.g., root, stem, leaf, flower, flower bulb, bark, fruit, seed, seed pod, sap whole plant etc.). In particular aspects, the combinations of skin actives identified in any one of Tables 2-6 are particularly interesting for use in multi-functional/multi-beneficial skin treatment compositions.

Example 4

Assays that Can Be Used To Test Compositions

The efficacy of compositions comprising the plant extracts identified throughout the specification, or a combination of such extracts (including, for example, the formulations identified in Tables 4-11), can be determined by methods known to those of ordinary skill in the art. The following are non-limiting assays that can be used in the context of the present invention. It should be recognized that other testing procedures can be used, including, for example, objective and subjective procedures.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a formula containing any one, or any combination thereof, of the extracts identified throughout the specification. Repeat measurements are taken at regular intervals to determine the formula's ability to reduce redness, inflammation, or skin irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay: Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Matrix Metalloproteinase Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon=13{,}600$ M$-1$ cm$-1$ at pH 6.0 and above 7). * * * * * * * * * * * * *

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A method of treating a skin condition resulting from exposure to pollution or free radicals, the method comprising topically applying to skin having the skin condition a composition comprising an effective amount of an extract of *Diospyros mespiliformis* leaf to reduce oxidative damage in the skin having the skin condition.

2. The method of claim 1, wherein the skin condition is a fine line or wrinkle.

3. The method of claim 1, wherein the skin condition is skin having reduced elasticity or firmness.

4. The method of claim 1, wherein the composition comprises from 0.01% to 20% by weight of the extract.

5. The method of claim 1, wherein the composition is a lotion or a cream.

6. The method of claim 1, wherein the composition is a gel or a serum.

7. The method of claim 1, wherein the composition is an emulsion.

8. The method of claim 7, wherein the composition is an oil-in-water emulsion.

9. The method of claim 1, wherein the *Diospyros mespiliformis* leaf extract also increases collagen production in the skin.

10. The method of claim 1, wherein the *Diospyros mespiliformis* leaf extract also reduces COX-1, MMP-1, tyrosinase, or TNF-α activity in the skin.

11. The method of claim 1, wherein the extract is an aqueous extract.

12. The method of claim 1, wherein the extract is an alcoholic extract.

13. The method of claim 1, wherein the extract is an aqueous-alcoholic extract.

14. The method of claim 1, wherein the composition further comprises a moisturizing agent or a humectant.

15. The method of claim 1, wherein the composition further comprises at least 40% by weight of water.

16. The method of claim 1, wherein the pollution is environmental pollution.

17. The method of claim 1, wherein the pollution is air pollution.

18. The method of claim 1, wherein the composition further comprises:
water;
xanthan gum;
disodium EDTA;
capryl glycol; and
C12-15 alkyl benzoate.

19. The method of claim 1, wherein the composition further comprises:
water;
glycerin;
butylene glycol;
phenoxyethanol;
disodium EDTA; and
potassium sorbate.

20. The method of claim 19, wherein the composition further comprises
dimethicone;
capryl glycol; and
maltodextrin.

* * * * *